United States Patent [19]

Wowk

[11] 3,933,680

[45] Jan. 20, 1976

[54] STABILIZING COMPOSITIONS FOR POLYVINYLCHLORIDE

[75] Inventor: Anatole Wowk, Edison, N.J.

[73] Assignee: M & T Chemicals Inc., Greenwich, Conn.

[22] Filed: July 16, 1971

[21] Appl. No.: 163,451

Related U.S. Application Data

[63] Continuation-in-part of Ser. No. 43,230, June 3, 1970, abandoned.

[52] U.S. Cl............................ 252/406; 260/45.75 S
[51] Int. Cl.$^2$............................................. C08J 3/20
[58] Field of Search............... 252/406; 260/45.75 K

[56] References Cited
UNITED STATES PATENTS

| | | | |
|---|---|---|---|
| 2,914,506 | 11/1959 | Mack et al. | 260/45.75 |
| 3,542,825 | 11/1970 | Hoye | 260/45.75 |
| 3,565,931 | 2/1971 | Brecker | 260/45.75 |

*Primary Examiner*—V. P. Hoke
*Attorney, Agent, or Firm*—Robert P. Auber; Kenneth G. Wheeless; Robert Spector

[57] ABSTRACT

This invention relates to novel compounds, oligomers, and polymers exhibiting at least one direct carbon to tin bond, at least one direct halogen to tin bond, at least one direct oxygen to tin bond, and at least one direct sulfur to tin bond, methods of preparing these novel compounds, and to polymers stabilized against the deteriorative effects of heat and light by two component compositions comprised at least in part of the novel compounds of this invention.

1 Claim, No Drawings

STABILIZING COMPOSITIONS FOR POLYVINYLCHLORIDE

This application is a continuation-in-part of application Ser. No. 43,230, filed June 3, 1970 now abandoned. This invention relates to novel organotin compounds and to novel stabilized halogen-containing polymer compositions.

Halogen-containing polymers, including homopolymers and copolymers of vinyl chloride and vinylidene chloride, are materials which have proven useful, because of their desirable physical properties. Uses of these materials have been limited, however, by their inherent instability when exposed to conditions of heat and light. Under such conditions, the halogen-containing polymer may discolor, become brittle, crack, check or otherwise suffer deterioration of its physical properties. Thus, unstabilized chlorine-containing polymer compositions may be highly unsatisfactory for outdoor use where they may be subjected to both heat and light. Various techniques are known for stabilizing these polymers against degradation in the presence of heat alone or light alone but no single stabilizer compound has been found which confers the high degree of both heat and light stability which is required for outdoor use.

A further defect of prior art stabilizers is that they may normally be viscous liquids or pasty gels. They may thus be considerably more difficult to handle than solid stabilizers.

It is an object of this invention to provide novel organotin compounds which may be characterized by their unexpectedly superior physical properties. It is a further object of this invention to provide novel chlorine-containing polymer compositions characterized by their high resistance to degradation during outdoor exposure.

One aspect of this invention relates to novel compounds exhibiting one direct carbon to tin bond, one direct halogen to tin bond and one direct sulfur to tin bond and one direct oxygen to tin bond.

This invention also relates to halogen-containing polymers stabilized against the deteriorative effects of heat and light comprising a halogen-containing polymer and an effective amount of a stabilizer composition comprised at least in part of compounds, oligomers, and polymers exhibiting at least one direct carbon to tin bond, at least one direct halogen to tin bond, at least one direct oxygen to tin bond, and at least one direct sulfur to tin bond.

The novel compounds of this invention include those of the formula:

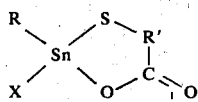

wherein X is chlorine or bromine and R and R' are hydrocarbons as hereinafter defined.

The novel oligomers and polymers of this invention are those of the formula:

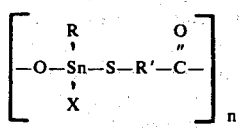

wherein X is chlorine or bromine and $n$ is an integer of from 2 to 20.

The novel compounds of this invention may be prepared by reacting a compound of the formula $RSn(OH)_2X$ wherein R is a hydrocarbon radical selected from the group consisting of alkyl, alkenyl, cycloalkyl, aralkyl, aryl, and alkaryl and X is chlorine or bromine with a mercapto acid of the formula

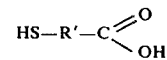

or suitable derivative thereof, e.g. the corresponding acid anhydride.

In the foregoing formulae R is a monovalent hydrocarbon radical selected from the group consisting of alkyl, aralkyl, alkaryl, and aryl radicals containing up to 20 carbon atoms and cycloalkyl radicals containing 5 to 8 carbon atoms. When R is an alkyl radical it may be a straight chain alkyl or a branched alkyl, including methyl, ethyl, n-propyl, isopropyl, n-butyl, isobutyl, sec-butyl, tert-butyl, n-amyl, neopentyl, isoamyl, n-hexyl, isohexyl, heptyls, octyls, decyls, dodecyls, tetradecyl, octadecyl, etc. When R is cycloalkyl, it may typically be cyclopentyl, cyclohexyl, cycloheptyl or cyclooctyl. R may represent a bicyclic hydrocarbon radical, e.g. bicyclo [2,2,0] hexane. When R is aralkyl, it may typically be benzyl, β-phenylethyl, γ-phenylpropyl, β-phenylpropyl, etc. When R is aryl, it may typically be phenyl, naphthyl, etc. When R is alkaryl, it may typically be tolyl, xylyl, p-ethylphenyl, p-nonylphenyl, etc. R may be inertly substituted, e.g. may bear a non-reactive substituent such as alkyl, aryl, cycloalkyl, aralkyl, alkaryl, ether, etc.

R' is a divalent hydrocarbon radical selected from the group consisting of alkylene, arylene, alkarylene and aralkylene radicals containing up to 20 carbon atoms and cycloalkylene radicals containing 5 to 8 carbon atoms. The radicals which R' can represent include the divalent equivalents of all radicals specified for R in the preceding paragraph.

Preferred novel compounds of this invention include: monobutylmonochlorotin S,O mercaptoacetate, monooctylmonochlorotin S,O mercaptoacetate, monocyclohexylmonochlorotin S,O mercaptoacetate, monomethylmonochlorotin S,O mercaptoacetate, monophenylmonochlorotin S,O mercaptoacetate, monobutylmonochlorotin S,O mercaptopropionate, monooctylmonochlorotin S,O mercaptopropionate, monocyclohexylmonochlorotin S,O mercaptopropionate, monomethylmonochlorotin S,O mercaptopropionate, monophenylmonochlorotin S,O mercaptopropionate, monobutylmonochlorotin S,O ortho-mercaptobenzoate and the corresponding monoorganomonobromotin compounds.

The reactant $RSn(OH)_2X$ of this invention is prepared from the compound $RSnX_3$. Typical compounds $RSnX_3$ include, but are not limited to, the following: ethyltin trichloride, propyltin trichloride, n-butyltin trichloride, hexyltin trichloride, octyltin trichloride, phenyltin trichloride, o-tolyltin trichloride, benzyltin trichloride, butenyltin trichloride, ethynyltin trichloride, and each of the corresponding tribromides.

Compounds such as butyltin bromide dichloride may be employed, most preferably the compound $RSnX_3$ is a chloride; and the preferred compounds are n-butyltin trichloride and n-octyltin trichloride. The process for preparing the compound $RSn(OH)_2X$ includes maintaining an aqueous reaction mixture containing $RSnX_3$; adding to said reaction mixture a catalytic amount of a catalyst selected from the group consisting of aluminum chloride, titanium tetrachloride, bismuth trichloride, ferric chloride, cobalt chloride, nickel chloride, cadmium chloride, zirconium tetrachloride, boron trifluoride etherate, mercuric chloride, cupric chloride, trifluoroacetic acid, and zinc fluoride; thereby forming a precipitate containing $RSn(OH)_2X$; and recovering said precipitate from said aqueous reaction mixture. In practice, 10–200 parts, say 17.5 parts of $RSnX_3$ are added to 100 parts of aqueous reaction medium, preferably water. Catalyst, preferably aluminum chloride, is added in an amount of 0.1–10 parts, say 0.95 parts, and the solution allowed to stand for up to 2–3 hours. The solid precipitate which forms may be separated as by filtration and washed with 10–1000 parts, say 15 parts of water. After further washing with 6–60 parts, say 12 parts of e.g. acetone, the precipitate may be air-dried. The product, typically obtained in an amount of 2.5 parts, is recovered from the filtrate.

The reaction $RSnX_3 + 2OH^- \rightarrow RSn(OH)_2X + 2X^-$ includes maintaining an aqueous reaction mixture containing $RSnX_3$; adding to said aqueous reaction mixture base in an amount not stoichiometrically greater than the amount of $RSnX_3$ thereby forming a precipitate containing $RSn(OH)_2X$; and recovering said precipitate from said aqueous reaction mixture. In practice, 10–100 parts of $RSnX_3$ may be added to 100 parts of aqueous reaction medium, preferably water. Base, preferably an alkali metal hydroxide such as potassium hydroxide, sodium hydroxide may be added thereto preferably as a solution containing 1–50 parts, say 10 parts of base in 100 parts of water. The amount of base added should not be stoichiometrically greater than, and preferably equal to, the amount of $RSnX_3$, i.e. two equivalents of base per mole of $RSnX_3$. The product $RSn(OH)_2X$ may precipitate and, preferably after standing for 4–12 hours be separated as by filtration. The precipitate may be washed with 50–500 parts, say 200 parts of water (which has been acidified preferably with hydrochloric acid) to pH of preferably about 2.0. The product may then be dried.

The process for preparing $RSn(OH)_2X$ when R is alkyl includes maintaining an aqueous reaction mixture containing $RSnX_3$; heating said reaction mixture thereby forming a precipitate containing $RSn(OH)_2X$ product; and recovering said precipitate from said aqueous reaction medium. In practice, 1–40 parts, say 4 parts of $RSnX_3$ may be added to 100 parts of aqueous reaction medium, preferably water. The reaction mixture may then be heated to 70°C–120°C, preferably to reflux temperature for 1–5 hours, preferably 2 hours.

The product $RSn(OH)_2X$ may copiously precipitate and be recovered by filtration. The precipitate may be washed with 2–10 parts, say 5 parts of water (which preferably has been acidified preferably with hydrochloric acid to pH of preferably 2.4). The product may be further washed with acetone (acidified to pH of 2.4) and air-dried.

Typical preferred reactants $RSn(OH)_2X$ include but are not limited to the following: ethyltin chloride dihydroxide, propyltin chloride dihydroxide, n-butyltin chloride dihydroxide, isobutyltin chloride dihydroxide, hexyltin chloride dihydroxide, octyltin chloride dihydroxide, phenyltin chloride dihydroxide, o-tolyltin chloride dihydroxide, benzyltin chloride dihydroxide, butenyltin chloride dihydroxide, and ethynyltin chloride dihydroxide. The corresponding bromide derivatives of the foregoing compounds are also suitable reactants.

Reaction mechanisms for the formation of the novel compounds, oligomers, and polymers of this invention are clearly illustrated by the following equations:

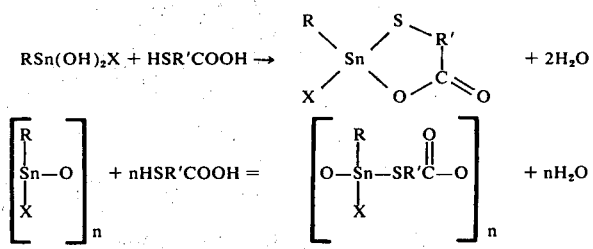

These equations graphically show that a reaction occurs between the mercapto acid and the polymer or compound $RSn(OH)_2X$ whereby water splits off and a chemical bond is formed between the tin and sulfur. These equations further illustrate the necessity of one molecule of the mercapto compound per mole of the compound $RSn(OH)_2X$ to obtain the desired reaction and the desired novel compound having a 1:1 molar ratio of sulfur to tin.

It is within the scope of this invention that pure, impure or commercial grades of the reactants may be employed satisfactorily. In general, pure compounds of the above formulae may be prepared from pure raw materials. However, these novel compounds may be diluted with innocuous, inert materials thereby permitting the use of technical grades of materials or intermediates in their preparation.

Any suitable reaction temperatures may be employed. It is ordinarily preferred to use room or slightly elevated temperatures of the order up to about 100°C. The exothermic nature of the reaction between the compound $RSn(OH)_2X$ and the sulfur containing compounds affords a considerable saving in the expenditure of external heat. The presence of water produced by the condensation reaction usually requires an additional heating or refluxing in order to strip said water from the reaction product, though it may be removed in any suitable matter.

The use of inert organic solvents as a medium for a reaction such as toluene, benzene, other aromatics, etc., is contemplated. The presence of such solvent facilitates the desired reaction. The solvent may be eliminated from the reaction product at the completion of the reaction by any suitable means. This may be accomplished by vaporizing the solvent under vacuum at elevated temperatures. Pressures of about 2 to 30 mm of mercury at temperatures of 75°C to 160°C are satisfactory in affecting the removal of toluene or like solvent from the reaction product.

By these procedures, the novel compounds of this invention can be obtained in almost theoretical yields. These yields are indicative that it is not necessary to use an excess of either reactant, the total amount of starting materials being substantially utilized in the formation of the final reaction product.

Polymers or resins which may be stabilized by practice of this invention are halogen-containing organic polymers typically those which contain chlorine atoms bonded to the polymer chain. These polymers include polyvinyl chloride-type polymers, e.g. polyvinyl chloride, polyvinylidene chloride, etc. They may also include copolymers formed by the copolymerization of vinyl chloride or vinylidene chloride with each other or with other ethylenically unsaturated monomers. Ethylenically unsaturated monomers may be compounds which contain polymerizable carbon-to-carbon double bonds and may include acrylates such as acrylic acid, ethyl acrylate, acrylonitrile, etc.; vinyl monomers such as styrene, vinyl acetate, etc.; maleates such as maleic acid, maleic anhydride, maleate esters, etc.

The polymers may be either "rigid" or "flexible". When "rigid" polymers are employed, they may include impact modifiers, pigments and/or fillers, lubricants, etc., in addition to the resin and stabilizer. When "flexible" polymers are employed, they may include plasticizer (primary and secondary), pigments and/or fillers, lubricants, etc., in addition to the resin and stabilizer.

In general the synthetic resins which can be stabilized according to this invention include the following polymers which may or may not be mixed with other stabilizers, additives, flameproofing agents, dyes, pigments, etc.:

a. Homopolymer of vinyl chloride,
b. Homopolymer of vinylidene chloride,
c. Copolymers of vinyl chloride and acrylonitrile,
d. Copolymers of vinylidene chloride and acrylonitrile,
e. Copolymers of vinylidene chloride, acrylonitrile and N-isopropylacrylamide,
f. Copolymers of vinyl chloride and vinyl acetate,
g. Copolymers of vinyl chloride, acrylonitrile, and N-butyrylacrylamide,
h. Copolymers of vinyl chloride, methyl methacrylate and vinyl acetate,
i. Copolymers of vinyl chloride or vinylidene chloride with acrylonitrile and N-vinylpyridine,
j. Copolymers of vinyl chloride or vinylidene chloride with acrylonitrile mixed with a homopolymer of an N-alkylacrylamide (e.g. N-iso-propylacrylamide, N-octylacrylamide, etc.),
k. Copolymers of vinyl chloride or vinylidene chloride with acrylonitrile mixed with a homopolymer or copolymer of α-vinylpyrrolidone,
l. Copolymers of vinyl chloride or vinylidene copolymers of an N-alkylacrylamide and acrylonitrile,
m. Other copolymers and mixtures of homopolymers or copolymers of vinyl chloride and/or vinylidene chloride with or without other monoolefinically unsaturated polymerizable monomers containing from 2 to 20 or more carbon atoms, especially those containing from 2 to 8 carbon atoms and no more than one nitrogen atom and no more than 2 oxygen atoms.

The methods for preparing the synthetic resins described above are well known and such methods and a great variety of such synthetic resins are described in the prior art. These synthetic resins are useful in preparing fibers, films, molding compositions, coating materials, wrapping materials, electrical insulation, fabrics, rope, plastic, pipe, paints, laminating materials for safety glass, adhesives, etc. Synthetic resins as stabilized in accordance with this invention are especially advantageous in synthetic fibers and products made therefrom such as rugs, wearing apparel, draperies, seat covers, upholstery, rope, cigarette filters, etc. Resistance to weathering (e.g. moisture and ultraviolet light) is especially important for items exposed to out of doors conditions. Resistance to ultraviolet light is also important for rugs, draperies, automobile seat covers, porch furniture upholstery and the like which may receive considerable sunlight.

The following examples are for illustration and are not to be construed as limiting the scope of the invention.

EXAMPLE 1

Preparation of monobutylmonochlorotin S,O mercaptopropionate and/or the polymer thereof.

Monobutylmonochlorotin S,O mercaptopropionate and the polymeric derivative were prepared by adding 24.55 grams (0.10 moles) of butylchlorotin dihydroxide and 10.6 grams (0.1 moles) of 3-mercaptopropionic acid to 120 milliliters of benzene contained in a reaction vessel equipped with a stirrer, a thermometer and a reflux condenser over a Dean-Stark trap. After water was removed by azeotropic distillation (at 84.5°) the benzene solvent was removed under reduced pressure leaving a residue which was dried to yield a product exhibiting a weight of 31.2 grams. Analysis of the product indicated the following:

| Elemental Percentage of | Calculated | Found |
|---|---|---|
| Sn | 37.6 | 37.12 |
| S | 10.16 | 9.86 |
| Cl | 11.25 | 10.39 |

EXAMPLE 2

Preparation of polymer monobutylmonochlorotin S,O mercaptopropionate.

Monobutylmonochlorotin S,O mercaptopropionate was prepared by adding 10.6 grams (0.10 moles) of 3-mercaptopropionic acid to 22.75 grams (0.10 moles) of polymeric butylchlorotin oxide in 275 milliliters of benzene.

Butyl chlorotin dihydroxide (22.75 grams) was slurried with 125 ml benzene in a 500-ml flask (round-bottomed 3-necked) equipped with stirrer, thermometer, and a reflux condenser over a Dean-Stark trap. The white slurry was heated to reflux, refluxed (79°-83°) for 2 hours to azeotrope water out. The theoretical amount of water (1.8 ml) was collected in the trap while the white solid dissolved. The dehydrated organotin compound was diluted with additional 150 ml benzene and mercaptopropionic acid was added. A milky reaction mix was reheated to reflux and refluxed for 1¼ hours (80.5°C). In this time 2.0 ml water was removed by azeotropic distillation and the mixture became clear and colorless. This solution was concentrated under reduced pressure until a glassy residue was obtained which was then dried in a vacuum oven at 50°–55°C for 3 ½ hours. The glassy solid product exhibited a weight of 32.2 grams and the following analysis, by weight:

| Elemental Percentage of | Calculated | Found |
|---|---|---|
| Sn | 37.6 | 37.12 |
| S | 10.16 | 9.82 |
| Cl | 11.25 | 10.65 |
| Cl/Sn Atomic Ratio | 1.00 | 0.96 |

EXAMPLE 3

Preparation of monobutylmonochlorotin S,O ortho-mercaptobenzoate.

Monobutylmonochlorotin S,O ortho-mercaptobenzoate was prepared by adding 30.8 grams (0.20 moles) of ortho-mercaptobenzoic acid and 49.1 grams (0.2 moles) of butyltin dihydroxychloride to 350 milliliters of benzene. The process was conducted as disclosed in Example 1. The product exhibited a weight of 69.8 grams, a 98% yield, and the following elemental analysis:

| Elemental Percentage of | Calculated | Found |
|---|---|---|
| Sn | 32.67 | 32.37 |
| S | 8.82 | 8.41 |
| Cl | 9.76 | 9.35 |

EXAMPLE 4

Preparation of monooctylmonochlorotin S,O mercaptopropionate.

The novel compound monooctylmonochlorotin S,O mercaptopropionate was prepared by adding 21.2 grams (0.2 moles) of mercaptopropionic acid and 60.3 grams (0.2 moles) of octyltin dihydroxychloride to 200 milliliters of benzene in a one liter reaction vessel equipped with a stirrer, a thermometer, and a reflux condenser. The by-product water was removed by azeotropic distillation while the reaction mixture was heated to reflux temperature for one hour. The benzene solvent was removed under reduced pressure. The product exhibited a weight of 78.0 grams and the following elemental analysis:

| Elemental Percentage of | Calculated | Found |
|---|---|---|
| Sn | 31.96 | 32.14 |
| S (metal bonded) | 8.63 | 8.40 |
| Cl | 9.54 | 9.30 |

The novel compounds of this invention are useful as one ingredient of two-component stabilizers for halogen-containing polymers. Typically the stabilizer compositions are used in an amount of 0.05 to 10 parts by weight of 100 parts by weight of halogen-containing, typically vinyl chloride, resins. Preferably they may be used in the amount of 0.25–3, per 100 parts of halogen-containing resin. Thus the preferred heat-stable vinyl chloride polymer compositions of this invention comprise 100 parts by weight of a vinyl chloride polymer and a stabilizing amount, typically 0.05–10 parts of a novel compound of this invention. The second component of the stabilizer composition is preferably a diorganotin S,S' bis(dimercaptide) or a diorganotin S,S' bis(dimercaptocarboxylate) of the general formulae $R_2{}^1Sn(SR^2)_2$ and $R_2{}^1Sn(SR^3COOR^2)_2$, respectively. $R^1$ and $R^2$ are monovalent hydrocarbon radicals selected from the same group as R and $R^3$ is selected from the same group as $R'$, all as described hereinbefore.

It is a feature of the novel stabilizer systems of this invention that it permits attainment of stabilized halogen-containing polymers and resins, particularly vinyl halide polymers such as vinyl chloride characterized by their resistance to the deteriorative effect of heat. The degrees of stabililzation attained in such systems may be considerably in excess of that previously attainable by any prior art stabilizer system.

Because of the outstanding properties of this novel stabilizer system, it is often possible to effect stabilization with lower quantities and thereby to obtain a more effective system on a cost-performance basis.

In order to illustrate clearly the novel features of this aspect of this invention and to illustrate the unexpected and outstanding results which may be attained by practice of this invention, the following illustrative examples may be set forth wherein all parts are parts by weight unless otherwise indicated.

In these examples, the rigid vinyl chloride polymer employed was that having a specific gravity of 1.40, a Shore Durometer "D" hardness of 80 and an ultimate tensile strength of about 7,000 psi sold under the trademark Geon 103 EP (or equivalent).

The novel compounds employed were monobutylmonochlorotin S,O mercaptopropionate; monobutylmonochlorotin S,O mercaptoacetate; and monobutylmonochlorotin S,O mercaptobenzoate. The second stabilizer components were dibutyltin S,S' bis(isooctyl mercaptoacetate), di-n-butyltin S,S' bis(isooctyl mercaptopropionate) and di-n-butyltin S,S' di(lauryl mercaptide).

The polymer-stabilizer mixture was thoroughly blended using a two-roll differential speed mill wherein the rolls were oil-heated to a temperature of 175°C. The mixtures were milled for about 5 minutes. A continuous band of the composition formed around one of the rolls. This band was cut and the composition was removed from the hot roll as a continuous sheet. Squares of this material measuring 2.54 cm × 2.54 cm were cut for heat stability testing.

For the heat stability test, the squares were placed in an air oven regulated to maintain a temperature of 190°C. Samples of each composition were removed from the oven at 15 minute intervals and were rated visually as to color change and degradation according to the following scale:

7 - clear, water-white
6 - off-white
5 - Slightest degree of yellowing
4 - definite yellow color
3 - deep yellow-brown color
2 - deep brown color
1 - dark brown to black color The length of time in minutes required to reach a value of 3 or less was recorded as the Heat Stability Value.

The Heat Stability Value does not provide an indication of color changes which occur during the early stages of the heat testing. A comparative rating system was therefore devised to obtain a more meaningful representation of the color changes which occurred during the first 60 minutes of the heat exposure period and to establish a criterion for comparing heat stabilities of polymer samples containing the compounds of the instant invention in combination with di-n-butyltin S,S' bis(isooctyl mercaptoacetate) or other control stabilizer with a sample containing only the control stabilizer.

The comparative rating was obtained by calculating the average of the 5 color ratings (including the rating prior to heat treatment) observed at each of the 15 minute intervals during 60 minutes of heat exposure, dividing the average by the average obtained for the control alone and multiplying the quotient by 100.

The Heat Stability Value and comparative stability rating for each of the polymer samples tested are recorded in the following table. For the sake of brevity each of the stabilizers is represented by a letter, as follows:

A = monobutylmonochlorotin S,O mercaptobenzoate

B = monobutylmonochlorotin S,O mercaptoacetate

C = monobutylmonochlorotin S,O mercaptopropionate

D = di-n-butyltin S,S' bis(isooctyl mercaptoacetate) (control)

E = di-n-butyltin S,S' bis(isooctyl mercaptopropionate) (control)

F = di-n-butyltin S,S' di(lauryl mercaptide) (control)

The monobutylmonochlorotin S,O mercaptoacetate can be prepared using the procedure of Example 4 and substituting an equimolar amount of mercaptoacetic acid for the mercaptopropionic acid.

| Stabilizer | % By Weight (based on polymer) | Heat Stability Value (minutes) | Comparative Stability Rating |
|---|---|---|---|
| A[a] | 2.0 | 0[b] | — |
| B[a] | 2.0 | 0[b] | — |
| C | 2.0 | 15 | — |
| D (control) | 2.0 | 60 | 100 |
| E (control) | 2.0 | 75 | 100 |
| F (control) | 2.0 | 60 | 100 |
| A / D | 0.2 / 1.8 | 75 | 113 |
| A / E | 0.2 / 1.8 | 60 | 92 |
| A / F | 0.2 / 1.8 | 45 | 105 |
| B / D | 0.2 / 1.8 | 75 | 113 |
| B / E | 0.2 / 1.8 | 60 | 88 |
| B / F | 0.2 / 1.8 | 60 | 132 |
| C / D | 0.2 / 1.8 | 60 | 109 |

[a] 0.5% of a stearyl stearate wax added to prevent polymer from adhering to mill rollers
[b] Initial color rating = 2

The preceding data clearly demonstrate the unexpectedly superior stabilization imparted to poly(vinyl chloride) resins by the stabilizer compositions of this invention.

I claim:

1. A novel composition for stabilizing a homopolymer or copolymer of vinyl chloride against the deteriorative effects of heat which comprises (1) a first stabilizer selected from the group consisting of butylchlorotin S,O mercaptoacetate, butylchlorotin S,O mercaptopropionate and butylchlorotin S,O mercaptobenzoate and (2) a second stabilizer selected from the group consisting of dibutyltin S,S' bis (isooctyl mercaptoacetate) and dibutyltin S,S' di(lauryl mercaptide).

* * * * *